(12) United States Patent
Ito et al.

(10) Patent No.: US 10,379,077 B2
(45) Date of Patent: Aug. 13, 2019

(54) GAS SENSOR ELEMENT

(71) Applicant: DENSO CORPORATION, Kariya, Aichi-pref. (JP)

(72) Inventors: Makoto Ito, Kariya (JP); Takehiro Watarai, Kariya (JP)

(73) Assignee: DENSO CORPORATION, Kariya (JP)

( * ) Notice: Subject to any disclaimer, the term of this patent is extended or adjusted under 35 U.S.C. 154(b) by 76 days.

(21) Appl. No.: 15/528,119

(22) PCT Filed: Nov. 2, 2015

(86) PCT No.: PCT/JP2015/080868
§ 371 (c)(1),
(2) Date: May 19, 2017

(87) PCT Pub. No.: WO2016/080176
PCT Pub. Date: May 26, 2016

(65) Prior Publication Data
US 2017/0343505 A1    Nov. 30, 2017

(30) Foreign Application Priority Data

Nov. 19, 2014 (JP) .................................. 2014-234948
Jul. 13, 2015 (JP) .................................. 2015-139917

(51) Int. Cl.
*G01N 27/407* (2006.01)
*G01N 27/41* (2006.01)
(Continued)

(52) U.S. Cl.
CPC .......... *G01N 27/41* (2013.01); *G01N 27/409* (2013.01); *G01N 27/4072* (2013.01);
(Continued)

(58) Field of Classification Search
CPC .......... G01N 27/4071; G01N 27/4072; G01N 27/4077
See application file for complete search history.

(56) References Cited

U.S. PATENT DOCUMENTS 6,210,641 B1 * 4/2001 Yamada .............. F02D 41/0027
123/696
2011/0094883 A1    4/2011 Ito et al.

FOREIGN PATENT DOCUMENTS

JP    2012-093330    5/2012

OTHER PUBLICATIONS

Full EPO computer-generated English language translation of the Description section of Japanese patent JP 2012-9330 A. Downloaded Sep. 27, 2018. (Year: 2012).*

(Continued)

*Primary Examiner* — Alexander S Noguerola
(74) *Attorney, Agent, or Firm* — Nixon & Vanderhye P.C.

(57) ABSTRACT

A gas sensor element includes a main body having a solid electrolyte body on which a measurement gas-side electrode and a reference gas-side electrode are provided, a trap layer covering an outer peripheral surface of the main body to trap poisoning substances contained in a measurement gas, and a waterproof protective layer covering an outer peripheral surface of the trap layer. In the protective layer, there is formed at least one measurement gas introduction port for introducing the measurement gas to the measurement gas-side electrode via the trap layer.

6 Claims, 7 Drawing Sheets

(51) Int. Cl.
*G01N 27/409* (2006.01)
*G01N 33/00* (2006.01)
G01N 1/22 (2006.01)
G01N 33/497 (2006.01)

(52) U.S. Cl.
CPC ..... *G01N 27/4077* (2013.01); *G01N 33/0047* (2013.01); *G01N 2001/2244* (2013.01); *G01N 2033/4975* (2013.01)

(56) References Cited

OTHER PUBLICATIONS

English translation of International Search Report dated Jan. 26, 2016, issued in corresponding Application No. PCT/JP2015/080868 (1 page).

\* cited by examiner

GAS SENSOR ELEMENT

CROSS-REFERENCE TO RELATED APPLICATIONS

This application is the U.S. national phase of International Application No. PCT/JP2015/080868 filed Nov. 2, 2015, which designated the U.S. and claims priority to Japanese Patent Application No. 2014-234948 filed on Nov. 19, 2014 and Japanese Patent Application No. 2015-139917 filed on Jul. 13, 2015, the contents of each of which are hereby incorporated by reference in their entireties into this application.

TECHNICAL FIELD

The present invention relates to a gas sensor element for sensing the concentration of a specific component in a measurement gas (i.e., gas to be measured).

BACKGROUND ART

In the exhaust system of an internal combustion engine of a motor vehicle, there is arranged a gas sensor for sensing the concentration of a specific component (e.g., the concentration of oxygen) in the exhaust gas which is the measurement gas.

Such a gas sensor has a gas sensor element built therein. The gas sensor element includes, for example, a solid electrolyte body having oxygen ion conductivity, a measurement gas-side electrode provided on one surface of the solid electrolyte body, a reference gas-side electrode provided on the other surface of the solid electrolyte body, and a porous diffusion-resistant layer which covers the measurement gas-side electrode and which allows the measurement gas to permeate therethrough. The gas sensor element is used in a state of having been heated to a high temperature (e.g., not lower than 500° C.) at which the solid electrolyte body can be activated. Therefore, when water condensate contained in the exhaust gas intrudes into the gas sensor element and adheres to the high-temperature solid electrolyte body, a large thermal shock may be applied to the solid electrolyte body, causing water-induced cracking to occur.

To solve the above problem, there is disclosed, for example in Patent Document 1, a gas sensor element which has a structure for improving the resistance to water damage. Specifically, the gas sensor element has its outer peripheral surface covered with a protective layer; the protective layer is formed of a porous material which is permeable to the exhaust gas and dense. By setting the surface roughness Ra of the protective layer to be lower than or equal to 3.0 µm, the protective layer is hydrophilic at room temperature and water-repellent at high temperature. Consequently, it is possible to prevent the adherence of water droplets to the gas sensor element at high temperature, thereby suppressing water-induced cracking from occurring.

PRIOR ART LITERATURE

Patent Literature

[Patent Document 1] Japanese Patent No. JP5287807B2

SUMMARY OF THE INVENTION

However, the inventors of the present application have found that the gas sensor element disclosed in Patent Document 1 involves the following problems.

When the properties of fuel combusted in an internal combustion engine are inferior, the fuel contains many poisoning substances such as Mn, Fe, Ca and the like. Moreover, when these poisoning substances are exhausted along with the exhaust gas and adhere to the protective layer, it may become impossible to keep the surface roughness Ra of the protective layer lower than or equal to 3.0 µm, thereby disabling the protective layer from being water-repellent at high temperature. Consequently, the resistance of the gas sensor element to water damage may be lowered and thus water may intrude into the gas sensor element.

Moreover, in recent years, with the strengthening of exhaust gas regulations, it has been desired to promptly detect, during the starting of an internal combustion engine, the concentration of a specific component in the exhaust gas by a gas sensor element. Therefore, it is necessary to promptly increase the temperature of the solid electrolyte body to an activation temperature; thus a quick temperature increase is made by a heater. However, when water has intruded into the gas sensor element and is heated by the quick temperature increase, the water will be vaporized and expanded to become water vapor. In the gas sensor element disclosed in Patent Document 1, the protective layer is permeable to gases such as the exhaust gas; however, when gases permeate through the protective layer, there occurs a flow resistance. Hence, when the rate of pressure increase due to the vaporization and expansion of the water is high with respect to the speed at which the water vapor permeates through the protective layer and is exhausted, the pressure inside the gas sensor element will become high so that the gas sensor element may be damaged.

The present disclosure has been made in view of the above circumstances and aims to provide a gas sensor element which is superior in both resistance to water damage and resistance to poisoning and capable of suppressing damage during a quick temperature increase.

In an embodiment of the present disclosure, a gas sensor element includes:

a main body including a solid electrolyte body having oxygen ion conductivity, a measurement gas-side electrode provided on one surface of the solid electrolyte body and a reference gas-side electrode provided on the other surface of the solid electrolyte body;

a trap layer formed of a porous material and covering an outer peripheral surface of the main body, the trap layer allowing a measurement gas to permeate therethrough while trapping poisoning substances contained in the measurement gas; and a protective layer covering an outer peripheral surface of the trap layer and having a water-impermeable property, wherein in the protective layer, there is formed at least one measurement gas introduction port for introducing the measurement gas to the measurement gas-side electrode via the trap layer.

With the above configuration, the gas sensor element includes the trap layer covering the outer peripheral surface of the main body and the protective layer covering the outer peripheral surface of the trap layer. Therefore, it is possible to improve both the resistance of the gas sensor element to water damage and the resistance of the gas sensor element to poisoning and suppress damage to the gas sensor element during a quick temperature increase.

Specifically, the protective layer is formed of a material having a water-impermeable property, such as a dense ceramic layer having an extremely low porosity. Therefore, the protective layer can be waterproof regardless of the surface properties thereof. Hence, even if poisoning substances contained in the exhaust gas have adhered to the protective layer, the waterproofness of the protective layer can be maintained without being lowered. Consequently, it becomes possible to prevent intrusion of water into the main body and improve both the resistance to water damage and the resistance to poisoning at the solid electrolyte body.

Moreover, in the protective layer, there is formed the measurement gas introduction port. Therefore, the path connecting the inside and the outside of the gas sensor element can be limited to the measurement gas introduction port. Consequently, it becomes possible to effectively suppress foreign substances, such as poisoning substances and water, from intruding into the gas sensor element. Furthermore, when water, which has intruded into the gas sensor element, is vaporized and expanded to become water vapor, it is possible to immediately exhaust the water vapor via the measurement gas introduction port. That is, with the measurement gas introduction port, it is possible to effectively perform both the introduction of the measurement gas from the outside and the exhaust of the water vapor from the inside of the gas sensor element. Consequently, it becomes possible to suppress increase in the pressure inside the gas sensor element, thereby preventing the gas sensor element from being damaged.

Moreover, between the protective layer and the main body, there is formed the trap layer. Therefore, foreign substances in the measurement gas which are brought into contact with the trap layer via the measurement gas introduction port, such as poisoning substances and water, can be separated from the measurement gas by the trap layer. Furthermore, water, which is brought into contact with the trap layer via the measurement gas introduction port, will be held in pores of the trap layer that is formed of the porous material. In this manner, by trapping foreign substances, such as poisoning substances and water, with the trap layer, it is possible to prevent these foreign substances from reaching the solid electrolyte body. Consequently, it becomes possible to suppress the solid electrolyte body from being poisoned or damaged by water.

As above, according to the present disclosure, it becomes possible to provide the gas sensor element which is superior in both resistance to water damage and resistance to poisoning and capable of suppressing damage during a quick temperature increase.

Moreover, in the above gas sensor element, it is preferable that: the main body further includes a porous diffusion-resistant layer that allows the measurement gas, which is introduced to the measurement gas-side electrode, to permeate therethrough; in the main body, there is formed a gas introduction passage for introducing the measurement gas to the measurement gas-side electrode via the porous diffusion-resistant layer; the gas introduction passage has a main body-side introduction port that opens on the outer peripheral surface of the main body; and the at least one measurement gas introduction port of the protective layer is formed at a position opposite to the main body-side introduction port from the outer side. In this case, it is possible to form the at least one measurement gas introduction port in the vicinity of the main body-side introduction port. Consequently, it is possible to shorten the flow path of the measurement gas from the at least one measurement gas introduction port to the main body-side introduction port, thereby improving the sensitivity of the gas sensor element.

EMBODIMENTS FOR CARRYING OUT THE INVENTION (First Embodiment)

A gas sensor element 1 according to the first embodiment will be described hereinafter with reference to FIGS. 1-3.

Figure 1:
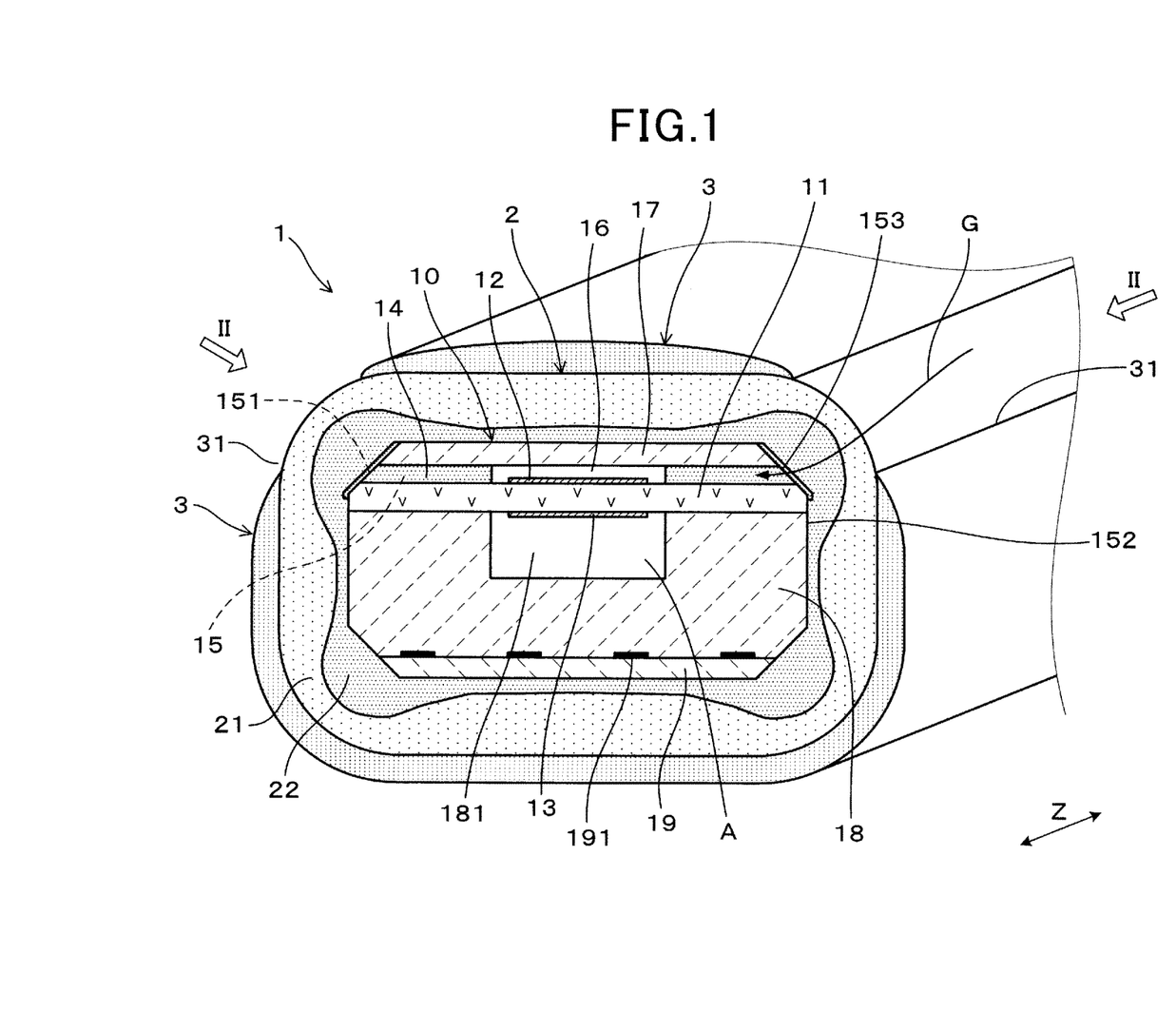
FIG. 1 is an explanatory diagram showing a gas sensor element according to a first embodiment.

As shown in FIG. 1, the gas sensor element 1 includes a main body 10, a trap layer 2 covering an outer peripheral surface 152 of the main body 10, and a protective layer 3 covering an outer peripheral surface of the trap layer 2.

The main body 10 includes a solid electrolyte body 11 having oxygen ion conductivity, a measurement gas-side electrode 12 provided on one surface of the solid electrolyte body 11, a reference gas-side electrode 13 provided on the other surface of the solid electrolyte body 11, and a porous diffusion-resistant layer 14 that allows a measurement gas G, which is introduced to the measurement gas-side electrode 12, to permeate therethrough.

The trap layer 2 is formed of a porous material that allows the measurement gas G to permeate therethrough. The trap layer 2 is provided to trap poisoning substances contained in the measurement gas G.

The protective layer 3 has a water-impermeable property (a waterproof property). In the protective layer 3, there are formed a pair of measurement gas introduction ports 31 for introducing the measurement gas G to the inside of the main body 10, more specifically to the measurement gas-side electrode 12 via the trap layer 2 and the porous diffusion-resistant layer 14.

Hereinafter, the configuration of the gas sensor element 1 will be described in more detail.

Figure 3:
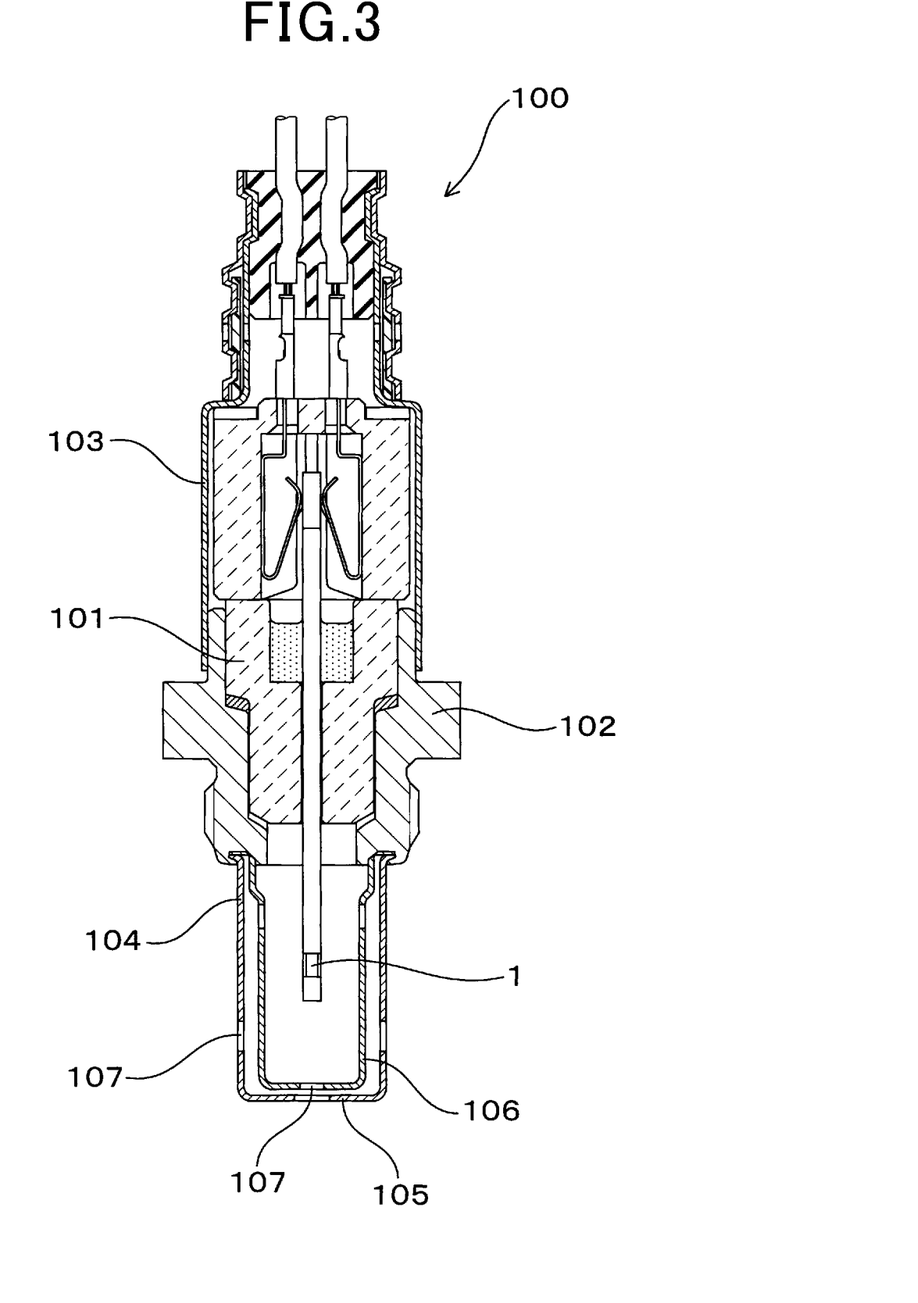
FIG. 3 is a cross-sectional view of a gas sensor which includes the gas sensor element according to the first embodiment.

As shown in FIG. 3, the gas sensor element 1 is employed in a gas sensor 100. The gas sensor 100 is configured as, for example, an A/F ratio sensor that detects the A/F (Air/Fuel) ratio of an air-fuel mixture supplied to an internal combustion engine of a motor vehicle based on the limit current flowing between the electrodes 12 and 13; the limit current depends on the concentration of oxygen in the exhaust gas (i.e., the measurement gas G) from the internal combustion engine.

The gas sensor 100 includes the gas sensor element 1, an insulator 101 that has the gas sensor element 1 inserted and held therein, a housing 102 that has the insulator 101 inserted and held therein, an atmosphere-side cover 103 provided on a proximal side of the housing 102, and an element cover 104 provided on a distal side of the housing 102 to protect the gas sensor element 1.

The element cover 104 is configured as a double cover consisting of an outer cover 105 and an inner cover 106. In side walls and bottom walls of the outer cover 105 and the inner cover 106, there are formed through-holes 107 through which the measurement gas G flows.

As shown in FIG. 1, in the gas sensor element 1, the solid electrolyte body 11 is formed of zirconia into a plate shape.

Both the measurement gas-side electrode 12 and the reference gas-side electrode 13 contain platinum.

On that surface of the solid electrolyte body 11 where the reference gas-side electrode 13 is provided, there is stacked a reference gas chamber formation layer 18. The reference gas chamber formation layer 18 is formed of alumina that is electrically insulative, dense and gas-impermeable. In the reference gas chamber formation layer 18, there is formed a groove-shaped reference gas chamber 181 into which a reference gas (e.g., atmospheric air) is introduced.

A heater substrate 19 is stacked on a surface of the reference gas chamber formation layer 18 opposite to the surface on which the solid electrolyte body 11 is arranged. The heater substrate 19 is formed of alumina. Between the reference gas chamber formation layer 18 and the heater substrate 19, there is embedded a heating element 191 that generates heat upon being energized. Moreover, by causing, through energization, the heating element 191 to generate heat, it is possible to quickly heat the gas sensor element 1 to an activation temperature.

On that surface of the solid electrolyte body 11 where the measurement gas-side electrode 12 is arranged, there is stacked the porous diffusion-resistant layer 14 on both sides of the measurement gas-side electrode 12. The porous diffusion-resistant layer 14 is formed of gas-permeable porous alumina.

A shield layer 17 is stacked on a surface of the porous diffusion-resistant layer 14 opposite to the surface on which the solid electrolyte body 11 is arranged. The shield layer 17 is formed of alumina that is electrically insulative, dense and gas-impermeable. That is, the porous diffusion-resistant layer 14 is provided between the solid electrolyte body 11 and the shield layer 17.

On that surface of the solid electrolyte body 11 where the measurement gas-side electrode 12 is provided, there are also formed a measurement gas chamber 16 and a gas introduction passage 15. The measurement gas chamber 16 is a space in which the measurement gas-side electrode 12 is arranged. The gas introduction passage 15 communicates with the measurement gas chamber 16 and guides the measurement gas G to the measurement gas chamber 16. The porous diffusion-resistant layer 14 is arranged in the gas introduction passage 15. Main body-side introduction ports 151, which are respectively located at ends of the gas introduction passage 15, open on the outer peripheral surface 152 of the main body 10. The measurement gas chamber 16 is surrounded by the shield layer 17, the porous diffusion-resistant layer 14 and the solid electrolyte body 11.

On each of the main body-side introduction ports 151 of the gas introduction passage 15, there is provided a catalyst layer 153 for removing hydrogen contained in the measurement gas G. The catalyst layer 153 is formed of a platinum-based catalyst.

The trap layer 2, which covers the outer peripheral surface 152 of the main body 10, is a porous layer formed of ceramic particles whose main component is γ-alumina or θ-alumina. Moreover, the trap layer 2 is configured to trap poisoning substances contained in the measurement gas G, such as chemical compounds produced from the components of an oil which include P, Si, Ca, and Zn.

The trap layer 2 is two layer-structured to include a first trap layer 21 and a second trap layer 22. The particle diameters and porosity of the first trap layer 21 are different from those of the second trap layer 22. In addition, the trap layer 2 may have a single layer structure or a structure of three or more layers.

The first trap layer 21 is formed of ceramic particles whose particle diameters are about 20 μm-40 μm and has a porosity of about 40%-80%. The first trap layer 21 is formed to cover the entire outer peripheral surface of the second trap layer 22. The cross-sectional shape of the first trap layer 21 is substantially rectangular ring-shaped.

The second trap layer 22 is formed of ceramic particles whose particle diameters are about 2 μm-8 μm and has a porosity of about 20%-70%. The second trap layer 22 is formed to cover the entire outer peripheral surface 152 of the main body 10. The second trap layer 22 is formed so that its thickness is partially increased at four corners of the main body 10.

In the first trap layer 21, of foreign substances such as poisoning substances, those which are relatively large and/or viscous are separated from the measurement gas G. Moreover, in the second trap layer 22, those small foreign substances which have passed through the first trap layer 21 are separated from the measurement gas G. Consequently, it is possible to prevent clogging in the trap layer 2 and efficiently introduce the measurement gas G to the measurement gas chamber 16.

Further, on the outside of the trap layer 2, there is formed the protective layer 3 to cover the trap layer 2. The protective layer 3 is a dense layer which is formed of ceramic particles whose main component is α-alumina and has a porosity of 5% or less.

In the protective layer 3, there are formed the pair of measurement gas introduction ports 31. Each of the measurement gas introduction ports 31 is formed at a position opposite to one of the main body-side introduction ports 151 of the gas introduction passage 15 from the outer side.

Figure 2:
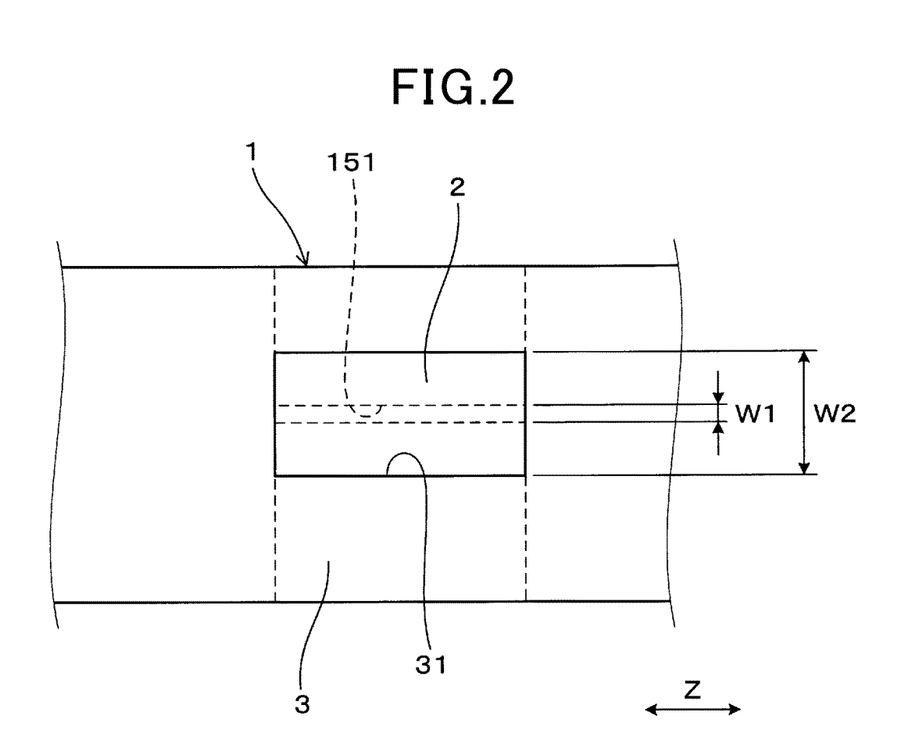
FIG. 2 is a view along arrows II in FIG. 1.

Moreover, as shown in FIG. 2, the measurement gas introduction ports 31 of the protective layer 3 are formed to have a width W2 of 0.5 mm. The measurement gas introduction ports 31 are formed so as to be long in a longitudinal direction Z of the gas sensor element 1. The width W2 denotes a width in a direction perpendicular to the longitudinal direction Z. The measurement gas introduction ports 31 may be formed to have the width W2 in the range of 0.5 mm-2.0 mm. If the width W2 of the measurement gas introduction ports 31 was less than 0.5 mm, the flow resistance of the measurement gas G introduced to the measurement gas chamber 16 would be high and thus might impede the flow of the measurement gas G. On the other hand, if the width W2 of the measurement gas introduction ports 31 was greater than 2.0 mm, it would be difficult to ensure the resistance of the gas sensor element 1 to water damage.

Moreover, the main body-side introduction ports 151 of the gas introduction passage 15 are formed to have a width W1 of 0.07 mm. The main body-side introduction ports 151 are formed so as to be long in the longitudinal direction Z of the gas sensor element 1. The width W1 denotes a width in the direction perpendicular to the longitudinal direction Z. The main body-side introduction ports 151 are formed within the range of the width W2 where the measurement gas introduction ports 31 are formed.

Next, advantageous effects achievable by the present embodiment will be described.

In the present embodiment, the gas sensor element 1 includes the trap layer 2 covering the outer peripheral surface 152 of the main body 10 and the protective layer 3 covering the outer peripheral surface of the trap layer 2. Therefore, it is possible to improve both the resistance of the gas sensor element 1 to water damage and the resistance of the gas sensor element 1 to poisoning and suppress damage to the gas sensor element 1 during a quick temperature increase.

Specifically, the protective layer 3 is formed of a material having a water-impermeable property. Therefore, the protective layer 3 can be waterproof regardless of the surface properties thereof. Hence, even if poisoning substances contained in the exhaust gas have adhered to the protective layer 3, the waterproofness of the protective layer 3 can be maintained without being lowered. Consequently, it becomes possible to prevent intrusion of water into the main body 10 and improve both the resistance to water damage and the resistance to poisoning at the solid electrolyte body 11.

Moreover, in the protective layer 3, there are formed the measurement gas introduction ports 31. Therefore, the path connecting the inside and the outside of the gas sensor element 1 can be limited to the measurement gas introduction ports 31. Consequently, it becomes possible to effectively suppress foreign substances, such as poisoning substances and water, from intruding into the gas sensor element 1. Furthermore, when water, which has intruded into the gas sensor element 1, is vaporized and expanded to become water vapor, it is possible to immediately exhaust the water vapor via the measurement gas introduction ports 31. That is, with the measurement gas introduction ports 31, it is possible to effectively perform both the introduction of the measurement gas G from the outside and the exhaust of the water vapor from the inside of the gas sensor element 1. Consequently, it becomes possible to suppress increase in the pressure inside the gas sensor element 1, thereby preventing the gas sensor element 1 from being damaged.

Moreover, between the protective layer 3 and the main body 10, there is formed the trap layer 2. Therefore, foreign substances in the measurement gas G which are brought into contact with the trap layer 2 via the measurement gas introduction ports 31, such as poisoning substances and water, can be separated from the measurement gas G by the trap layer 2. Furthermore, water, which is brought into contact with the trap layer 2 via the measurement gas introduction ports 31, will be held in pores of the trap layer 2 that is formed of the porous material. In this manner, by trapping foreign substances, such as poisoning substances and water, with the trap layer 2, it is possible to prevent these foreign substances from reaching the solid electrolyte body 11. Consequently, it becomes possible to suppress the solid electrolyte body 11 from being poisoned or damaged by water.

In the present embodiment, in the main body 10, there is formed the gas introduction passage 15 for introducing the measurement gas G to the measurement gas-side electrode 12 via the porous diffusion-resistant layer 14. The gas introduction passage 15 has the main body-side introduction ports 151 that open on the outer peripheral surface 152 of the main body 10. Each of the measurement gas introduction ports 31 of the protective layer 3 is formed at a position opposite to one of the main body-side introduction ports 151 of the gas introduction passage 15 from the outer side. Hence, it becomes possible to form each of the measurement gas introduction ports 31 in the vicinity of one of the main body-side introduction ports 151. Consequently, it becomes possible to shorten the flow path of the measurement gas G from the measurement gas introduction ports 31 to the main body-side introduction ports 151, thereby improving the sensitivity of the gas sensor element 1.

In the present embodiment, the measurement gas introduction ports 31 are formed within the range of the width W2 of 0.5 mm-2.0 mm. Therefore, it is possible to facilitate both the introduction of the measurement gas G and the exhaust of water vapor while effectively suppressing intrusion of water into the gas sensor element 1. Consequently, it becomes possible to effectively suppress increase in the pressure inside the gas sensor element 1 while further improving the resistance of the gas sensor element 1 to water damage.

As above, according to the present embodiment, it becomes possible to provide the gas sensor element 1 which is superior in both resistance to water damage and resistance to poisoning and capable of suppressing damage during a quick temperature increase.

(Second Embodiment)

Figure 4:
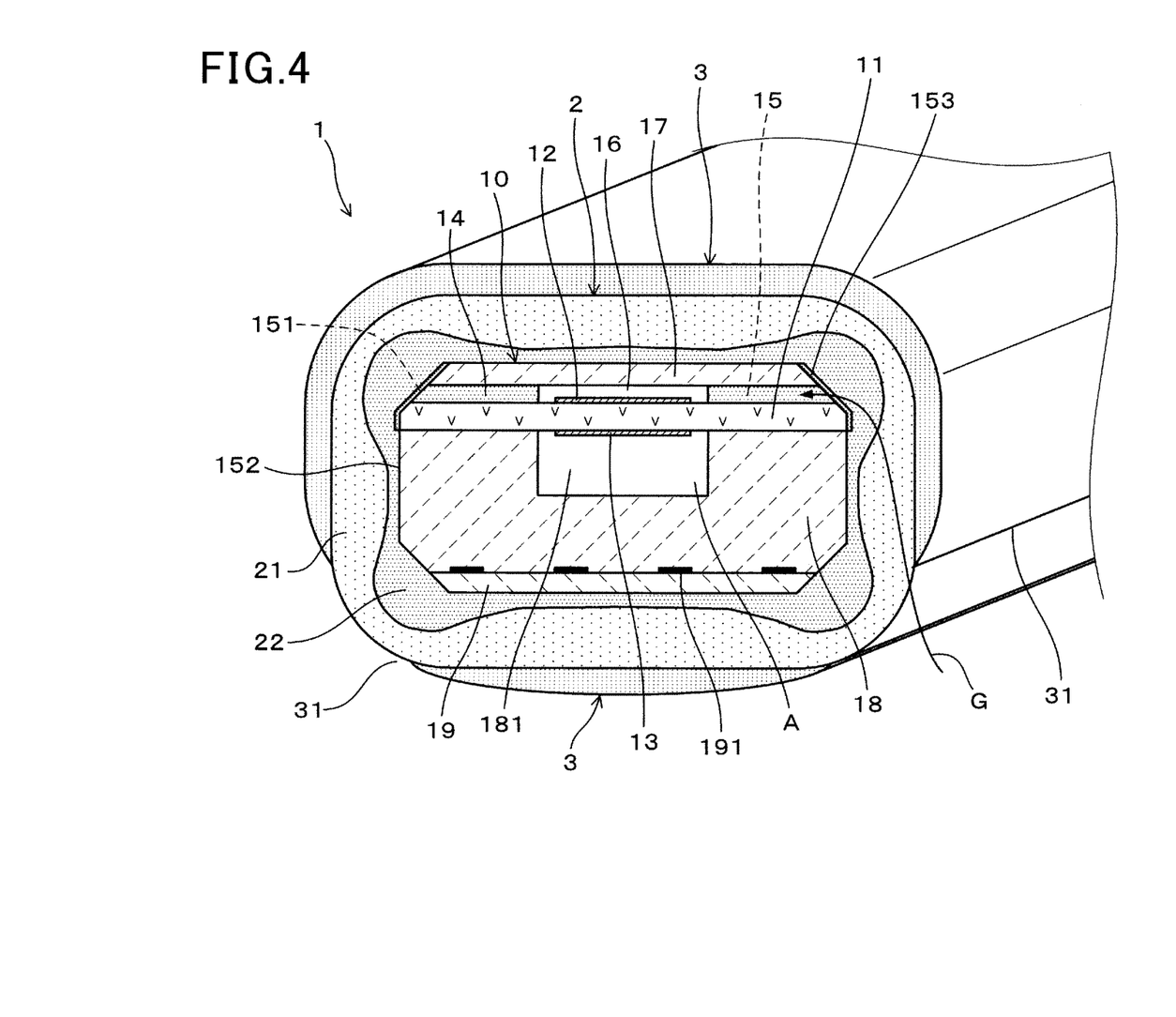
FIG. 4 is an explanatory diagram showing a gas sensor element according to a second embodiment.

In the present embodiment, as shown in FIG. 4, the formation positions of the pair of measurement gas introduction ports 31 of the protective layer 3 in the gas sensor element 1 of the first embodiment are modified. Specifically, in the present embodiment, the measurement gas introduction ports 31 of the protective layer 3 are formed at positions distant from the main body-side introduction ports 151 of the gas introduction passage 15. More specifically, the measurement gas introduction ports 31 are formed at positions respectively opposite to those corners of the main body 10 where no main body-side introduction ports 151 are formed.

In the present embodiment, other configurations and contents indicated by reference signs in the drawings are the same as in the first embodiment.

In the gas sensor element 1 according to the present embodiment, the distances from the measurement gas introduction ports 31 to the main body-side introduction ports 151 are increased in comparison with the case of the first embodiment. Thus, until reaching the main body-side introduction ports 151 from the measurement gas introduction ports 31, the measurement gas G passes through the trap layer 2 over longer distances. Therefore, it is possible to more effectively suppress intrusion of water and/or poisoning substances into the measurement gas chamber 16.

In addition, the measurement gas introduction ports 31 may be formed at various positions in the main body 10 according to the design conditions of the gas sensor element 1.

Moreover, according to the present embodiment, it is also possible to achieve the same advantageous effects as the first embodiment.

(Third Embodiment)

Figure 5:
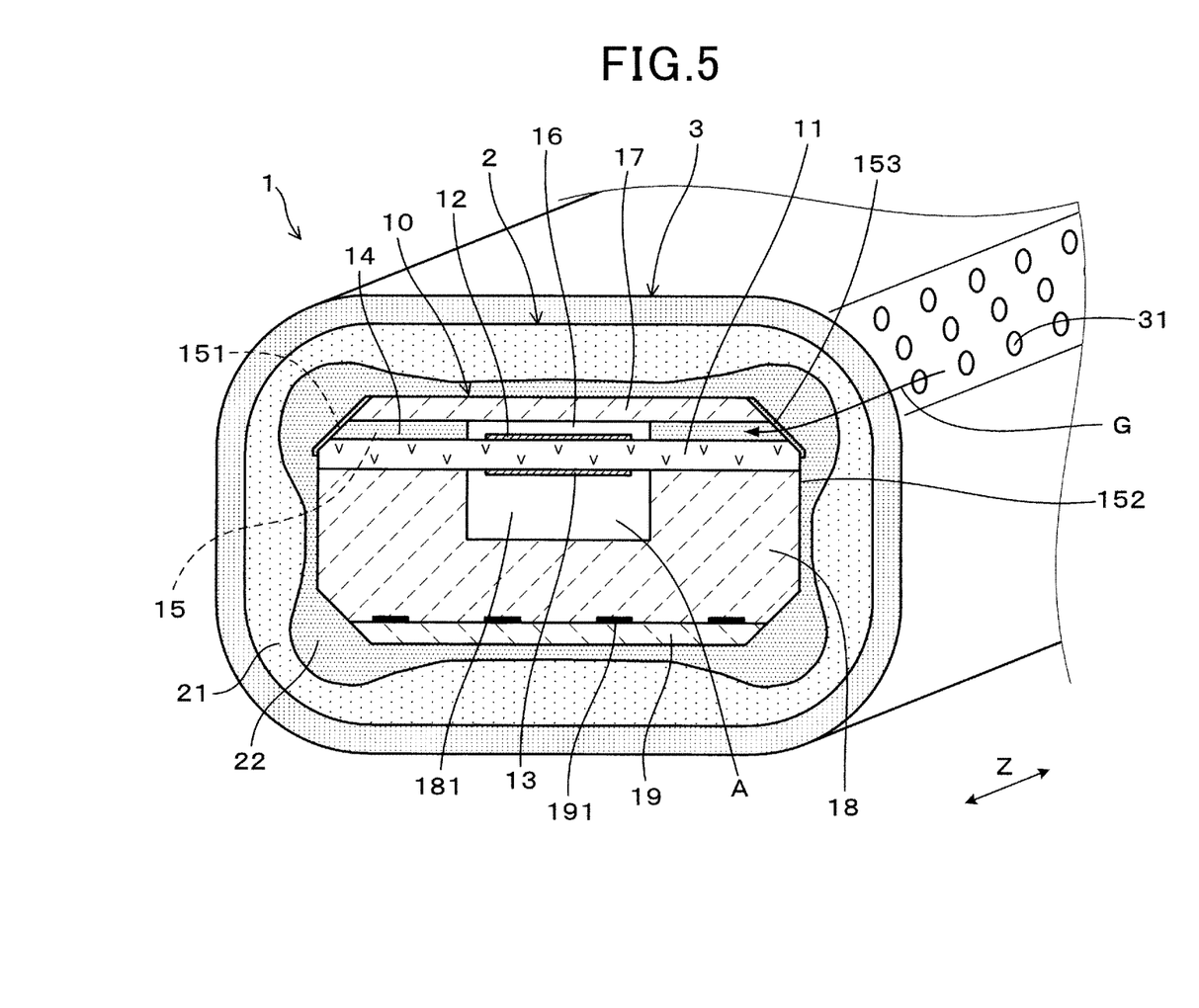
FIG. 5 is an explanatory diagram showing a gas sensor element according to a third embodiment.

In the present embodiment, as shown in FIG. 5, the formation manner of the pair of measurement gas introduction ports 31 of the protective layer 3 in the gas sensor element 1 of the first embodiment is modified. Specifically, in the present embodiment, each of the measurement gas introduction ports 31 of the protective layer 3 is formed of a number of through-holes of $\phi 0.01$ mm-$\phi 1.5$ mm. Moreover, the formation position of each of the measurement gas introduction ports 31 of the protective layer 3 is a position opposite to one of the main body-side introduction ports 151 as in the first embodiment. In addition, the formation position of each of the measurement gas introduction ports 31, which is formed of a number of through-holes, may also be set to various positions opposite to neither of the main body-side introduction ports 151.

In the present embodiment, other configurations and contents indicated by reference signs in the drawings are the same as in the first embodiment. Moreover, according to the present embodiment, it is also possible to achieve the same advantageous effects as the first embodiment.

(Fourth Embodiment)

Figure 6:
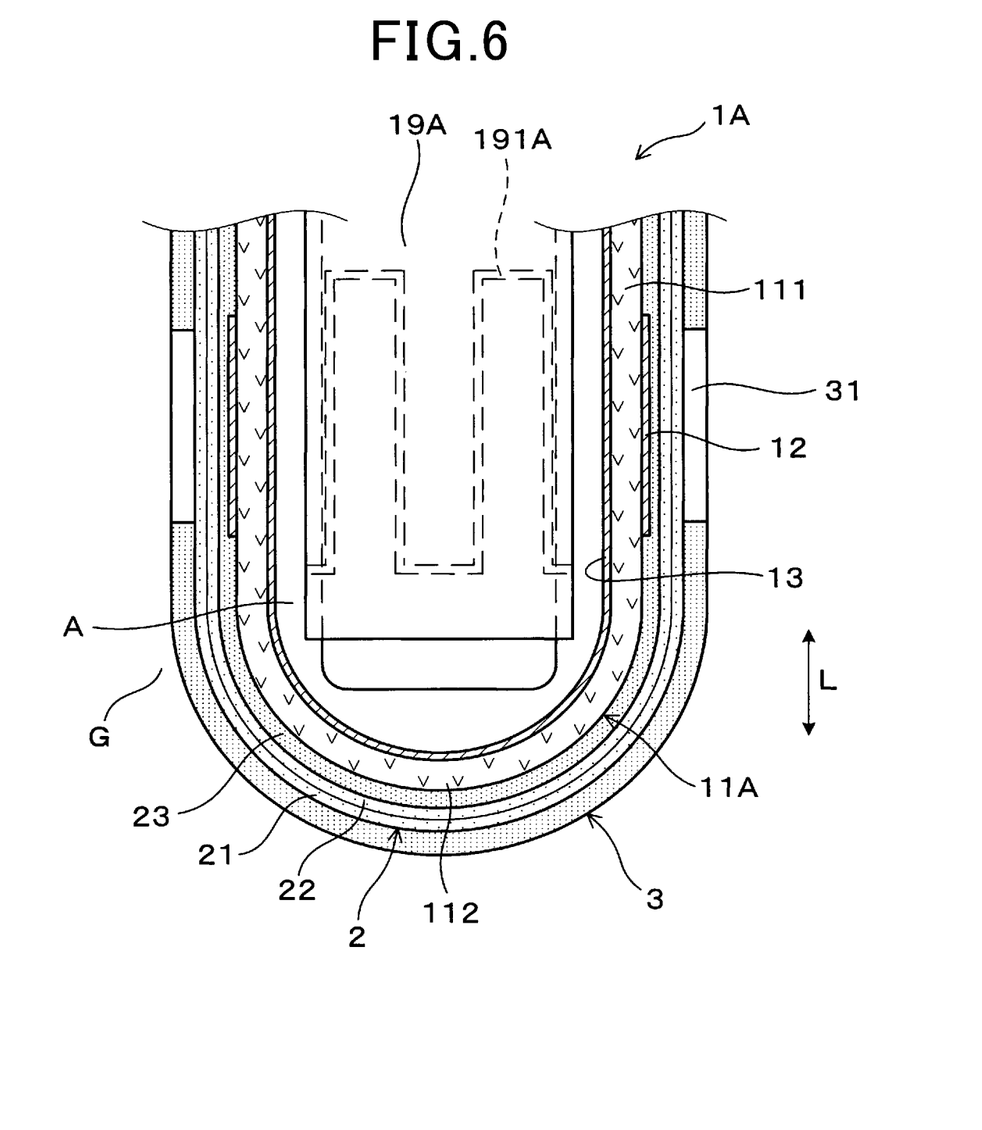
FIG. 6 is an explanatory diagram showing a gas sensor element according to a fourth embodiment.
Figure 7:
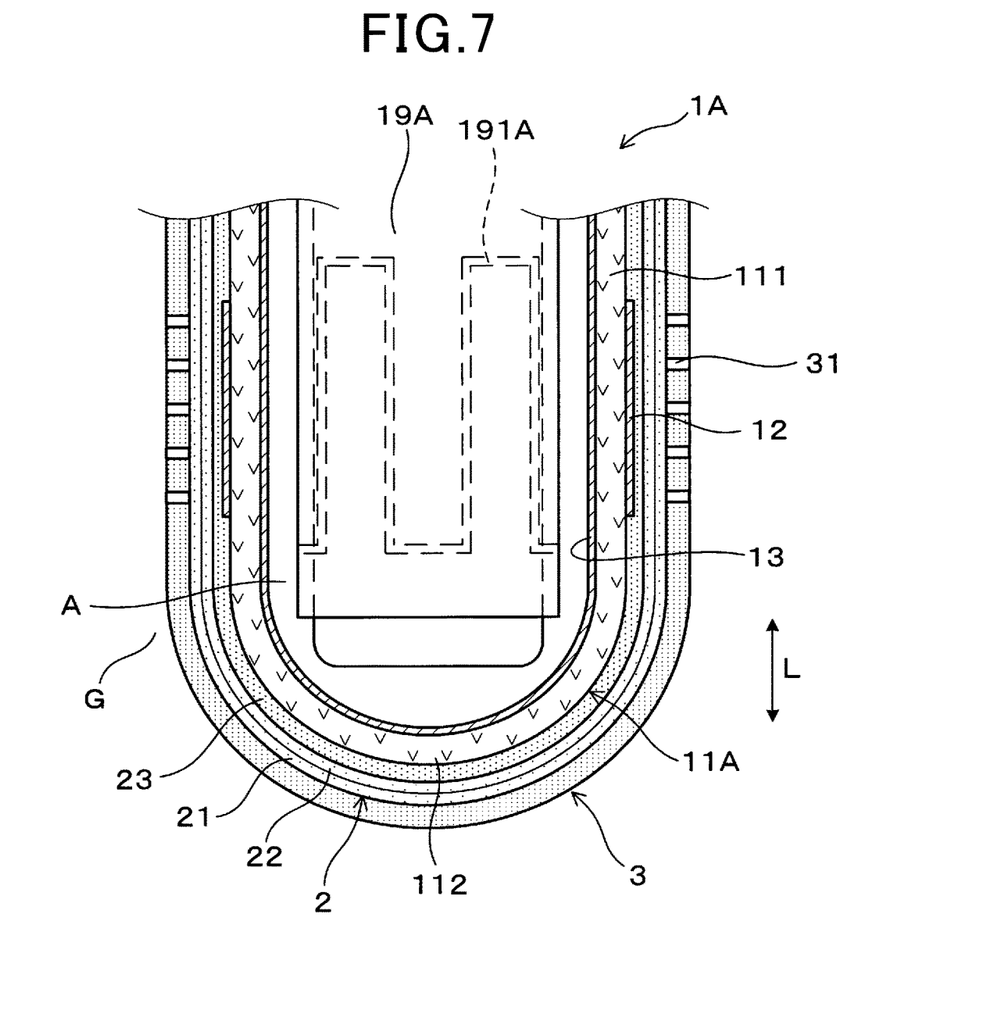
FIG. 7 is an explanatory diagram showing another gas sensor element according to the fourth embodiment.

As shown in FIGS. 6 and 7, this embodiment illustrates a gas sensor element 1A which employs a cup-shaped solid electrolyte body 11A instated of the plate-shaped solid electrolyte body 11.

The cup-shaped solid electrolyte body 11A is formed by closing an end of a cylindrical portion 111 with a hemispherical portion 112. A measurement gas-side electrode 12 is provided on an outer periphery of the cylindrical portion 111 of the solid electrolyte body 11A. A reference gas-side electrode 13 is provided on an inner periphery of the cylindrical portion 111 of the solid electrolyte body 11A.

On the outside of the solid electrolyte body 11A, there is provided an inner protective layer 23 for covering and thereby protecting the measurement gas-side electrode 12. The inner protective layer 23 is formed of a shock-absorbing material. Moreover, on the outside of the inner protective layer 23, there is provided a trap layer 2 that consists of a first trap layer 21 and a second trap layer 22. Furthermore, on the outside of the trap layer 2, there is provided a protective layer 3. In the protective layer 3, there are formed measurement gas introduction ports 31 at positions opposite to the measurement gas-side electrode 12.

The measurement gas-side electrode 12 may be provided over the entire circumference on the outer periphery of the solid electrolyte body 11A; the measurement gas introduction ports 31 may be provided at a plurality of locations which are spaced in a circumferential direction and opposite to the outer periphery of the solid electrolyte body 11A. The measurement gas introduction ports 31 may be formed into various shapes. For example, as shown in FIG. 6, the measurement gas introduction ports 31 may be formed so as to be long in an axial direction L of the solid electrolyte body 11A. Alternatively, as shown in FIG. 7, the measurement gas introduction ports 31 may be formed of a number of through-holes of $\phi 0.01$ mm-$\phi 1.5$ mm. In the case of forming the measurement gas introduction ports 31 with a number of through-holes, it is possible to form the through-holes so as to be distributed over the entire circumferential range opposite to the outer periphery of the solid electrolyte body 11A.

In the present embodiment, the measurement gas introduction ports 31 are formed at positions opposite to the measurement gas-side electrode 12 from the outer side. In addition, the measurement gas introduction ports 31 may also be formed at positions not opposite to the measurement gas-side electrode 12 from the outer side.

Moreover, in the present embodiment, a heater member 19A is arranged inside the solid electrolyte body 11A. The heater member 19A is formed of alumina and has a heating element 191A provided therein; the heating element 191A generates heat upon being energized.

In the gas sensor element 1A according to the present embodiment, by providing the protective layer 3 and the measurement gas introduction ports 31, it is possible to achieve the same advantageous effects as the gas sensor element 1 according to the first embodiment.

In addition, in the present embodiment, other configurations and contents indicated by reference signs in the drawings are the same as in the first embodiment.

In addition, the present disclosure is not limited to the above-described embodiments. It goes without saying that various modifications may be made without departing from the spirit of the present disclosure.

The invention claimed is:

1. A gas sensor element comprising:
a main body including a solid electrolyte body having oxygen ion conductivity, a measurement gas-side electrode provided on one surface of the solid electrolyte body and a reference gas-side electrode provided on the other surface of the solid electrolyte body;
a trap layer formed of a porous material and covering an outer peripheral surface of the main body, the trap layer allowing a measurement gas to permeate therethrough while trapping poisoning substances contained in the measurement gas; and
a protective layer covering an outer peripheral surface of the trap layer and having a water-impermeable property and a porosity of 5% or less, wherein
in the protective layer, there is formed at least one measurement gas introduction port for introducing the measurement gas to the measurement gas-side electrode via the trap layer.

2. The gas sensor element as set forth in claim 1, wherein:
the solid electrolyte body is plate-shaped,
the main body further includes a gas introduction passage, through which the measurement gas is introduced to the measurement gas-side electrode, and a porous diffusion-resistant layer arranged in the gas introduction passage,
the gas introduction passage has a main body-side introduction port that opens on the outer peripheral surface of the main body, and
the at least one measurement gas introduction port of the protective layer is formed to penetrate the protective layer and located to have the trap layer interposed between the at least one measurement gas introduction port and the main body-side introduction port.

3. The gas sensor element as set forth in claim 2, wherein a total cross-sectional area of the at least one measurement gas introduction port of the protective layer is greater than a total cross-sectional area of the main body-side introduction port.

4. The gas sensor element as set forth in claim 1, wherein the at least one measurement gas introduction port is formed within the range of a width of 0.5 mm-2.0 mm.

5. The gas sensor element as set forth in claim 1, wherein the trap layer is two-layer structured to include a first trap layer and a second trap layer,
the second trap layer is formed of ceramic particles to cover the outer peripheral surface of the main body and the first trap layer is formed of ceramic particles to cover an outer peripheral surface of the second trap layer,
a particle diameter of the ceramic particles forming the first trap layer is greater than a particle diameter of the ceramic particles forming the second trap layer, and
the second trap layer is formed so that its thickness is partially increased at four corners of the outer peripheral surface of the main body.

6. A gas sensor element comprising:
a main body including a cup-shaped solid electrolyte body having oxygen ion conductivity, a measurement gas-side electrode provided on an outer peripheral surface of the solid electrolyte body and a reference gas-side electrode provided on an inner peripheral surface of the solid electrolyte body;
a trap layer formed of a porous material and covering an outer peripheral surface of the main body, the trap layer allowing a measurement gas to permeate therethrough while trapping poisoning substances contained in the measurement gas; and
a protective layer covering an outer peripheral surface of the trap layer and having a water-impermeable property and a porosity of 5% or less, wherein in the protective layer, there is provided at least one measurement gas introduction port for introducing the measurement gas to the measurement gas-side electrode via the trap layer, and the at least one measurement gas introduction port is formed to penetrate the protective layer and located to have the trap layer interposed between the at least one measurement gas introduction port and the measurement gas-side electrode.

* * * * *